US012661037B2

(12) United States Patent
Lous et al.

(10) Patent No.:  US 12,661,037 B2
(45) Date of Patent:        Jun. 23, 2026

(54) OPTICAL MODULE

(71) Applicant: ams Sensors Germany GmbH, Jena (DE)

(72) Inventors: Erik Jan Lous, Veldhoven (NL); Peter Roentgen, Thalwil (CH); Remco Verdoold, Geldrop (NL)

(73) Assignee: ams Sensors Germany GmbH, Jena (DE)

( * ) Notice: Subject to any disclaimer, the term of this patent is extended or adjusted under 35 U.S.C. 154(b) by 408 days.

(21) Appl. No.: 18/284,481

(22) PCT Filed: Mar. 30, 2022

(86) PCT No.: PCT/EP2022/058429
§ 371 (c)(1),
(2) Date: Sep. 27, 2023

(87) PCT Pub. No.: WO2022/207713
PCT Pub. Date: Oct. 6, 2022

(65) Prior Publication Data
US 2024/0148286 A1      May 9, 2024

(30) Foreign Application Priority Data
Mar. 31, 2021     (GB) .................................... 2104630

(51) Int. Cl.
A61B 5/1455        (2006.01)
A61B 5/00          (2006.01)
(52) U.S. Cl.
CPC ............ A61B 5/1455 (2013.01); A61B 5/443 (2013.01); A61B 5/681 (2013.01);
(Continued)

(58) Field of Classification Search
CPC ...... A61B 2562/0242; A61B 2562/043; A61B 5/0059; A61B 5/0075; A61B 5/1455;
(Continued)

(56) References Cited

U.S. PATENT DOCUMENTS 6,352,502 B1 *   3/2002   Chaiken ............... A61B 5/0059
600/475
2001/0034478 A1   10/2001   Lambert et al.
(Continued)

FOREIGN PATENT DOCUMENTS

GB          2489717 A       10/2012
WO          99/63328 A1     12/1999
WO       2019/032735 A1      2/2019

OTHER PUBLICATIONS

International Search Report issued for corresponding International Patent Application No. PCT/EP2022/058429 on Jun. 24, 2022 (5 pages).
(Continued)

*Primary Examiner* — Chu Chuan Liu
(74) *Attorney, Agent, or Firm* — Viering, Jentschura & Partner mbB

(57)                ABSTRACT

An optical module for Raman spectroscopy includes a laser source mounted on a substrate and configured to emit electromagnetic radiation at a target. The optical module also includes a plurality of sensors mounted on the substrate and configured to detect electromagnetic radiation scattered from the target. The optical module further includes a first filter disposed over one or more of the plurality of sensors. The first filter is substantially transparent to a first wavelength band corresponding to a Raman scattering wavelength of a first molecule of the target and opaque to wavelengths outside the first wavelength band.

17 Claims, 12 Drawing Sheets

(52) U.S. Cl.
CPC ................. *A61B 2560/0443* (2013.01); *A61B 2562/0238* (2013.01); *A61B 2562/0242* (2013.01); *A61B 2562/043* (2013.01)

(58) Field of Classification Search
CPC ............ A61B 5/14551; A61B 5/14552; A61B 5/14532; A61B 5/6801; A61B 5/4875; A61B 5/681; A61B 5/6824
See application file for complete search history.

(56) References Cited

U.S. PATENT DOCUMENTS

| | | | | |
|---|---|---|---|---|
| 2004/0087832 | A1* | 5/2004 | Glukhovsky | A61B 5/073 600/118 |
| 2005/0027176 | A1 | 2/2005 | Xie | |
| 2005/0043597 | A1* | 2/2005 | Xie | A61B 5/1455 600/315 |
| 2006/0164635 | A1 | 7/2006 | Islam et al. | |
| 2007/0049831 | A1 | 3/2007 | Crowther et al. | |
| 2008/0129992 | A1* | 6/2008 | Matousek | A61B 5/0075 356/301 |
| 2013/0210058 | A1 | 8/2013 | White et al. | |
| 2013/0324819 | A1* | 12/2013 | Colvin, Jr. | A61B 5/14551 359/613 |
| 2014/0296665 | A1 | 10/2014 | Yamada | |
| 2021/0010865 | A1 | 1/2021 | Yang et al. | |
| 2023/0277063 | A1* | 9/2023 | Cucinelli | A61B 5/6826 600/310 |

OTHER PUBLICATIONS

Written Opinion issued for corresponding International Patent Application No. PCT/EP2022/058429 on Jun. 24, 2022 (9 pages).
Caspers et al., "In Vivo Confocal Raman Microspectroscopy of the Skin: Noninvasive Determination of Molecular Concentration Profiles", In Vivo Raman Spectroscopy of Skin, vol. 116, No. 3, Mar. 2001, pp. 434-442 (9 pages), cited in NPL Nos. 1 and 2 & Specification.
Search Report issued on Aug. 5, 2021 for corresponding Great Britain Patent Application No. GB2104630.5 (4 pages).

* cited by examiner

700

702

701

703

704

Hydration Level
76%
Past week plot

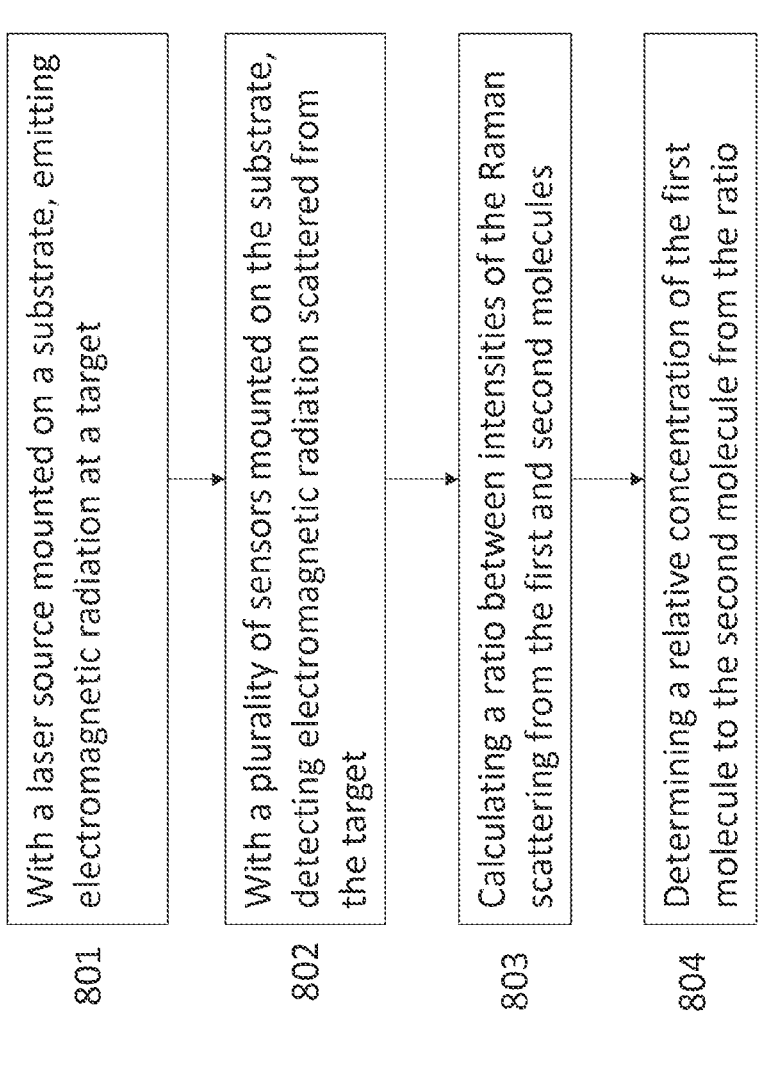

801  With a laser source mounted on a substrate, emitting electromagnetic radiation at a target 802  With a plurality of sensors mounted on the substrate, detecting electromagnetic radiation scattered from the target 803  Calculating a ratio between intensities of the Raman scattering from the first and second molecules 804  Determining a relative concentration of the first molecule to the second molecule from the ratio

OPTICAL MODULE

CROSS REFERENCE TO RELATED APPLICATION

This application is a National Stage of International Application No. PCT/EP2022/058429, filed on Mar. 30, 2022, which designates the United States and was published in Europe, and which claims priority to Great Britain Patent Application No. 2104630.5, filed on Mar. 31, 2021, in the Intellectual Property Office. All of the aforementioned applications are hereby incorporated by reference in their entireties.

FIELD

The present disclosure relates to an optical module for Raman spectroscopy and a method of use thereof.

BACKGROUND

Raman spectroscopy is a technique that utilizes monochromatic electromagnetic energy produced by, for example, a laser to determine vibrational modes of molecules. A laser emits photons of a known and fixed wavelength that strike molecules bringing their energy levels a virtual energy level state. After falling back from this state, the photon is scattered (emitted). When the energy levels of the laser emitted photon and the scattered photon correspond to each other ($\lambda_{scatter}=\lambda_{laser}$) the scattering is Rayleigh type scattering. Rayleigh scattering is the most observed type of scattering from an illuminated sample. A small fraction of the scattered photons will have a different photon energy and this type of scattering is Raman type scattering. In Raman scattering, a Stokes shift results in a higher wavelength number and anti-Stokes in a lower wavelength number.

If the illuminated sample contains a variety of different molecules, the observed Raman (Stokes and Anti-Stokes) scattering will have peaks spread over multiple wavenumbers and this may be visualized in a spectrum plot and analysed to identify the different molecules in the sample, each molecule being identifiable by the presence, position and strength of different peaks in the spectrum plot.

Known Raman spectrometers use a diffraction grating that divides the observed signal into multiple optical paths by wavelength, allowing the weaker Raman scattering signal to be isolated from the much stronger Rayleigh scattering signal. A line-pixel sensor may be connected to a lens to receive the Raman scattered light. A notch optical filter or a band pass filter may also be used to prevent the Rayleigh scattering component of the measured signal interfering with the much weaker Raman scattering component. A diffraction grating based optical setup such as this inevitably requires a minimum amount of space to ensure sufficient resolution is achieved when the diffraction grating divides the observed signal by wavelength. The greater the space requirements, the less a setup can be miniaturized.

One use of Raman spectroscopy is the determination of hydration levels of a patient. In the human body, and most vertebrates, water is used, for example, of the transportation of supplies and waste products and to carefully maintain a constant temperature in the body by using the advantage of the large heat capacity of water. However, an optimal hydration level allows the body to perform its functions efficiently and effectively. Slight over or under hydration will not immediately cause a problem due to the large amount of redundant systems the body has to cope with these problems. However, when over or under hydration exceeds certain levels it becomes dangerous and can result in death. Body hydration levels for most individuals with average daily routines will stay well within the safe levels. However, for those who undertake strenuous activities such as professional athletes, those who work in extreme environments such as firefighters, or those whose bodies are not able to self-regulate hydration for medical reasons such as the elderly or dialysis patients, hydration levels may need to be monitored to ensure they stay within safe limits. Monitoring hydration levels is challenging. Typically, hydration level is measured subjectively by performing a skin test. The skin between thumb and index finger is pulled up and released, the time and discoloration indicates the body hydration level. However, there are numerous factors influencing the outcome of this test e.g. skin composition, age and the person performing the test. Alternatively, urine color and volume can be measured to determine hydration levels, but vitamin uptake as well as minerals in the diet influences such measurements that can thus be inaccurate. The third common method is weight measurement, sometimes assisted by body impedance measurements. However, such measurements are also influenced by numerous external factors other than hydration.

A less subjective method of measuring hydration levels is using a Fresenius body composition monitor. This instrument measures the resistance differences between high and low frequency electrical current. High frequency current is able easily to pass through intra and extra cellular media where low frequency can only pass through extra cellular media. This can provide a more consistent body hydration level estimation and is often used to assess hydration levels in dialysis patients. However, the Fresenius body composition monitor can still have a high degree of inaccuracy in its measurements as numerous factors may effect current conduction in the human body.

A more objective way to measure hydration levels is to use Raman spectroscopy to identify OH molecule group signatures in a Rayleigh scattering from the dermis of a patient. Peter J. Caspers, Gerald W. Lucassen, Elizabeth A. Carter, Hajo A. Bruining, and Gerwin J. Puppels, (2001), "In Vivo Confocal Raman Microspectroscopy of the Skin: Noninvasive Determination of Molecular Concentration Profiles", 2001, VOL. 116, NO. 3 Mar. 2001, IN VIVO RAMAN SPECTROSCOPY OF SKIN by "The Society for Investigative Dermatology, Inc." (Caspers, 2001) proposes using a benchtop-sized diffraction grating based Raman spectrometer to determine water concentration in the dermis as a function of distance to the skin surface. In particular, at each probed depth under the skin surface, a ratio of the OH molecule concentration against the $CH_3$ molecule (present in biological dermis materials such as proteins) concentration may be determined by comparing the intensity of the Raman signal peaks ($I_{water}$) of OH molecules against the intensity ($I_{protein}$) of $CH_3$-based molecules. The ratio gives an estimate of water content percentage at each probed depth and thus gives an indication of the patient's hydration levels. FIG. 1a, taken from Caspers 2001, indicates known Raman spectra of a probed portion of skin showing peaks for $CH_3$ and OH molecules. The areas 101, 102 below each peak having Raman shifts between 2910-2965 $cm^{-1}$ for $CH_3$ and 3350-3550 $cm^{-1}$ for OH give an approximation of the $CH_3$ and OH concentration intensities $I_{protein}$ and $I_{water}$. Such measurements may be made at different depth levels under the skin, for example from 0-200 μm, and may be used to provide $I_{water}/I_{protein}$ ratio values for a plurality of different skin depths. FIG. 1b, taken from Caspers 2001, shows an example plot of different $I_{water}/I_{protein}$ values against skin depth for a plurality of different locations on a patient's skin indicating water content percentage against skin depth. Each different symbol indicates a different skin location. A typical hydration value is around 60-85% water content, depending on the location of the measurement on the patient's skin. For a heavily dehydrated patient, the water content percentage may be less. For an overly hydrated patient it may be more.

US2007/0049831A1 proposes a confocal Raman spectrometer with a diffraction grating for dermatological studies.

SUMMARY

According to one aspect of the disclosure there is provided an optical module for Raman spectroscopy, the optical module comprising: a laser source mounted on a substrate and configured to emit electromagnetic radiation at a target; a plurality of sensors mounted on the substrate and configured to detect electromagnetic radiation scattered from the target; and a first filter disposed over one or more of the plurality of sensors, wherein the first filter is substantially transparent to a first wavelength band corresponding to a Raman scattering wavelength of a first known molecule of the target and opaque to wavelengths outside the first wavelength band.

The optical module may further comprise a second filter disposed over one or more of the plurality of sensors, wherein the second filter is substantially transparent to a second wavelength band corresponding to a Raman scattering wavelength of a second known molecule of the target and opaque to wavelengths outside the second wavelength band.

Advantageously, the inventors have realized that when only the relative concentrations of a specific set of molecules in a target are of interest instead of a full molecular profile of the target, Raman spectroscopy may be performed without a diffraction grating because only a narrow band of the Raman shift spectrum (namely that associated with the Raman scattering of the chosen molecules) is of interest. These narrow bands can be isolated using filters without requiring a diffraction grating. In particular, known Raman spectrometers use a diffraction grating to divide the scattered signal components according to their wavelength. This allows known Raman spectrometers to be used to profile a full spectrum of potential molecular fingerprints. However, the use of a diffraction grating limits the scope for miniaturization as the smaller the spectrometer, the worse the resolution of the spectrometer is due to the diffraction grating being unable to resolve different wavelengths of the detected signal. In contrast, the inventors have realized that some applications of Raman spectroscopy do not require the determination of a full spectrum of molecular fingerprints.

For example, determination of a hydration level of a target such as the dermis layer of patient requires only the determination of the ratio of OH molecules (found in water) to $CH_3$ molecules (found in proteins and lipids in the dermis). Accordingly, only the narrow portion of the band of the spectrum of the scattered signal corresponding to these molecules is required.

Other similar applications to which the present disclosure is directed includes determining relative concentrations of other molecules or groups of molecules for example those found in glucose, blood, drugs, and others. In particular, these wavelength bands of interest can be isolated from the other components of the scattered signal without a diffraction grating using only filters. Omitting the diffraction grating and its associated optics from a Raman spectrometer simplifies the optical design, reduces the number of components required thereby reducing parasitics of otherwise more complex optical setups and electronic circuits. This allows to trade in optical resolution for more sensitivity. This allows for a more integrated solution where all components may be mounted to and integrated on a single substrate. This further allows for enhanced miniaturization compared to known Raman spectrometers. For example, the present disclosure enables a Raman spectrometer to be produced that has a volume of 20-100 $mm^3$ without a substantial reduction in resolution, something that is not possible to do with diffraction grating based Raman spectrometers. Miniaturized devices of the present disclosure may accordingly be wearable or integrated into wearable or mobile devices such as smart watches, smart phones, heart rate monitors, and other vital sign monitors in point-of-care environments and/or sport settings. The miniaturized devices of the present disclosure are accordingly cheaper to produce than larger, known Raman spectrometers with diffraction gratings and, by virtue of their integration on a single substrate, are suitable for mass production in semiconductor device fabrication facilities.

In one implementation, an integrated circuit is mounted on the substrate.

Advantageously, mounting an integrated circuit on the substrate further enhances the ease at which the device of the present disclosure may be mass-produced in semiconductor device fabrication facilities in high volumes compared to known Raman spectrometers which often require manual assembly which is slower and more expensive.

In one implementation, the integrated circuit is configured to control the laser source to emit modulated electromagnetic radiation at the target and demodulate the detected electromagnetic radiation scattered from the target.

Advantageously, as Raman scattering is a fast process, any modulation of, for example the frequency, amplitude, and/or phase of the laser source may also be detected in the scattered signal incident on the plurality of sensors. This allows for phase-locked detection of the modulation frequency in the Raman scattering signal, which further improves the sensitivity and accuracy of the detection of the Raman scattering signal. For example, sensitivity may be increased by 2-3 orders of magnitude independently of background environment lighting conditions (such as daylight). Accordingly, this allows the optical module to perform Raman spectroscopy in settings where lighting conditions cannot be easily be controlled such as point of care and sporting environments.

In one implementation, the integrated circuit accordingly comprises phase lock loop, amplification and laser source driver circuitry to provide the above increase in sensitivity. Advantageously, providing the phase lock loop, amplification and laser source driver circuitry on a single integrated circuit together with the plurality of sensors and filters also simplifies the electronic and optical design thereby reducing parasitic effects and noise compared to more complex circuits.

In one implementation, the integrated circuit is configured to calculate a ratio between intensities of Raman scattering from the first and second molecules, and the integrated circuit is further configured to determine a relative concentration of the first and second molecules from the ratio.

Advantageously, this allows the device of the present disclosure, which as described above, is simpler, cheaper, smaller and more cost effective than known Raman spectrometers, to be used to determine, for example, hydration level of the target, blood glucose level of the target, concentration of drug or other pharmacological compound in the target, and any other application where only relative concentration of specific, known molecules is required instead of a full molecular profile of the target.

In one implementation, the optical module comprises a lens, for example a fixed lens or variable lens, positioned in the optical path from the laser source to the target, the lens is configured to focus the electromagnetic radiation emitted by the laser source onto a one or more focal points at respective depths in a dermis layer of the target.

Advantageously, the lens allows multiple depths in a dermis layer to be probed thereby allowing a concentration profile as a function of target depth to be determined for example such as the hydration profiles shown in FIGS. 1a and 1b. The lens allows the focal point to be at accurate locations in the dermis under the skin of the target. At positions away from the focal points, for example, on the epidermis or pigment layer of the skin, the laser is out of focus and the power per unit area incident on out of focus points is reduced, thereby reducing the risk of accidental burns and damage to the skin. Where the lens is a variable lens, a single lens may be used to focus the emitted electromagnetic radiation at multiple focal points. Alternatively, multiple fixed lenses may be used, each focusing the emitted electromagnetic at a different focal point to obtain the full depth profile. Alternatively, if only a single focal point in in the target is of interest, a single fixed lens may be used. It is envisaged that any suitable arrangements of lens or lenses, fixed or otherwise may be used with the present disclosure.

In one implementation, the lens is positioned outside the optical path between the target and the plurality of sensors. The laser source is accordingly positioned spaced apart from the plurality of sensors on the substrate and is configured to emit the electromagnetic radiation out of the optical module at the target in a direction non-perpendicular to a plane of the substrate.

Advantageously, by positioning the laser source and the lens away from and out of the optical path from the target to the plurality of sensors and emitting the laser energy at the target at an angle relative to the substrate of the optical module and thus at an angle relative to the surface of the target, the power per unit area incident on the surface of target is further reduced thereby further reducing the risk of accidental burns and damage. Further, when the laser energy reaches the target surface, fluorescence may occur and this can introduce substantial noise in the detected signal. By positioning the laser source and lens away from and out of the optical path form the target to the plurality of sensors, any fluorescence that occurs is offset from the optical path from the target to the sensors, reducing the strength of any interference effect caused by the fluorescence.

Alternatively, in one implementation, the lens is positioned in the optical path between the target and the plurality of sensors and the optical module may comprise a plurality of reflectors. The reflectors are positioned in the optical path between the target and the plurality of sensors and are configured to direct the electromagnetic radiation scattered from the target to the plurality of sensors through the first and second filters Advantageously, this positioning of the lens allows it to be used as part of a collector system to focus the scattered electromagnetic radiation from the target onto the plurality of sensors thereby increasing the signal to noise ratio for very weak signals. Further, use of reflectors, such as mirrors, allows the lateral footprint and size of the optical module to be reduced.

In one implementation, the optical module comprises a plurality of laser sources mounted on the substrate and a plurality of lenses positioned in respective optical paths of the laser sources and configured to focus the emitted electromagnetic radiation from the laser sources onto the same focal point or a plurality of focal points at a plurality of depths in a dermis layer of the target.

Advantageously, in this implementation, multiple excitation sources in combination with the same focal point, allows each laser to have a reduced laser power compared to when a single laser source is used thereby ensuring sufficient excitation energy reaches the same focal point but each laser remains well below safety limits for skin illumination. Accordingly, the plurality of laser sources further divides the total laser power incident on the target surface over a much larger area further reducing the risk of accidental burns or damage to the target surface. In the case where the target is a user or patient's skin, the energy focused on the same focal point under the skin also stays well below the safety burn limits, which is helped by the fact that the path into the skin is already substantially attenuated as governed by Beer's Law. Very light skin colours are particularly vulnerable to such burns. Accordingly, this implementation allows the present disclosure to be used on users and patients who are at much higher risk of damage or burns than is possible with known Raman spectrometers. Further, the plurality of lenses may each have a different focus depth allowing the entire depth of the target to be profiled simultaneously and therefore be less dependent for different skin thicknesses or skin types or skin positions between different subjects/people.

In one implementation, the first and second filter respectively have an optical density value of between 6-16, preferably 8-14, more preferably 10-12, for example 11, for wavelengths outside the first and second wavelength bands.

Advantageously, filters of high optical density values of this arrangement completely attenuate all portions of the signal outside the wavelength bands to which the filter is transparent. Unlike in known Raman spectrometers where it is essential that almost the entire Raman spectrum is allowed to reach the sensors to ensure a full molecular fingerprint profile may be determined, the present disclosure attenuates not only the excitation source laser light but also almost the entire Raman spectrum except for the specific wavelength bands of interest. The filters thus ensure the excitation source is sufficiently attenuated such that only the required Raman wavelengths are sensed.

In one implementation, the electromagnetic radiation emitted by the laser source has a wavelength of between 600-785 nm (although a broader range of 500-900 nm is also envisaged); the first filter is transparent to a wavelength band corresponding to a Raman scattering wavelength of an OH molecule; and the second filter is transparent to a wavelength band corresponding to a Raman scattering wavelength of a $CH_3$ molecule.

Advantageously, as the target molecules are known, the laser source may be a single narrowband source designed to match the specific target molecule of interest. The laser emission wavelength of this implementation causes a good Raman scattering signal, for example, a Stokes or anti-Stokes Raman shift, from the OH and $CH_3$ molecules of the target. The filters of this implementation accordingly ensure almost the entire rest of the spectrum of the Raman scattering signal is attenuated allowing only the OH and $CH_3$ molecule components of the Raman scattering signal to reach the sensors. The intensities of the OH and $CH_3$ molecule components of Raman scattering signal may accordingly be used to determine a relative concentration of 7                                                                8

OH to CH₃ molecules thereby allowing a hydration level of the target to be determined in accordance with the methods described in Caspers 2001.

According to a second aspect of the present disclosure, there is provided, a method of determining relative concentrations of first and second known molecules of a target, the method comprising: with a laser source mounted on a substrate, emitting electromagnetic radiation at a target; with a plurality of sensors mounted on the substrate, detecting electromagnetic radiation scattered from the target, wherein first and second filters are disposed over the sensors, the first filter substantially transparent to a first wavelength band corresponding to a Raman scattering wavelength of the first molecule and opaque to wavelengths outside the first wavelength band, and the second filter substantially transparent to a second wavelength band corresponding a Raman scattering wavelength of the second molecule and opaque to wavelengths outside the second wavelength band; and calculating a ratio between intensities of the Raman scattering from the first and second molecules; and determining a relative concentration of the first molecule to the second molecule from the ratio.

Advantageously, as described above, the method of the present disclosure allows Raman spectroscopy to be performed without the use of a diffraction grating, thereby allowing the relative concentrations of first and second molecules of a target to be determined more cheaply and with a miniaturized device.

In one implementation of the method, the emitted electromagnetic radiation has a wavelength of between 600-785 nm (although a broader range of 500-900 nm is also envisaged); wherein the first filter is transparent to a wavelength band corresponding to a Raman scattering wavelength of an OH molecule; and wherein the second filter is transparent to a wavelength band corresponding to a Raman scattering wavelength of a CH₃ molecule. Accordingly, the first molecule is an OH molecule, the second molecule is a CH₃ molecule and the method comprises determining a hydration level of the target from the relative concentration of OH molecules to CH₃ molecules. These wavelength bands correspond to Raman shifts of 2910-2965 $cm^{-1}$ for CH₃ and 3350-3550 $cm^{-1}$ for OH and the specific wavelength band used will depend on the excitation wavelength as will be understood by the skilled person.

Advantageously, as described above, this implementation of the method allows hydration level of a target to be determined cheaply and with a miniaturized device.

According to a third aspect, there is provided, a Raman spectrometer comprising the optical module of any of the implementations described above, optionally the Raman spectrometer may comprise a computer-readable storage medium having stored thereon instructions which, when the instructions are executed by a processor, cause the processor to perform the method of any of the implementations described above.

Advantageously, such a Raman spectrometer is cheaper, simpler, smaller, and easier to mass-produce than known Raman spectrometers due to the user of the optical module of the present disclosure.

According to a fourth aspect, there is provided a wearable device comprising the optical module of any of the implementations described above, the wearable device may comprise, for example, one of a smart watch, a heartrate monitor, or a pulse-oximeter. Optionally, the wearable device may comprise a computer-readable storage medium having stored thereon instructions which, when the instructions are executed by a processor, cause the processor to perform the method of any of the implementations described above.

According to a fifth aspect, there is provided a hydration level monitor comprising the optical module of any of the implementations described above. Optionally, the hydration level monitor may comprise a computer-readable storage medium having stored thereon instructions which, when the instructions are executed by a processor, cause the processor to perform the method of any of the implementations described above.

Advantageously, providing the optical module of the present disclosure in a wearable device and/or in a hydration level monitor allows the device to be Raman spectroscopy enabled and thus allows Raman spectroscopy to be used in scenarios and applications where this was previously not possible due to the size limitations of desktop sized equipment and Raman spectrometers with a diffraction grating. In the case of hydration level determination, the hydration level monitor and/or wearable device of the present disclosure thus advantageously provide the high degree of accuracy of Raman spectroscopy for hydration level determination directly in point-of-care environments or during sporting events that is not currently possible using known Raman spectrometers or with known hydration determination techniques. For example, where the wearable device is a smartwatch sized device worn with an area of around 5×5 cm and height of 0.5-1 cm worn on the wrist, the optical module of the present disclosure (which may have a volume smaller than 20-100 mm³) may easily be incorporated into the device. As described above, this is made possible by omitting the typical Raman spectrometer diffraction grating and its associated optical components.

As described below, whilst the present disclosure details two Raman wavelengths and a hydration measurement, it is envisaged that the present disclosure can be extended to multiple Raman wavelengths and the determination of other types of molecules by comparing mutual intensity ratios of the filtered Raman signals. Further, whilst the target of human skin is given as an example, it is envisaged that the present disclosure may be used on many other types of targets Depending on the application of use.

BRIEF DESCRIPTION OF THE DRAWINGS

These and other aspects of the present disclosure will now be further described, by way of example only, with reference to the accompanying figures in which:

FIG. 8 is a flowchart of a method according to the present disclosure.

Like elements are indicated by like reference numerals.

DETAILED DESCRIPTION

Figure 1A:
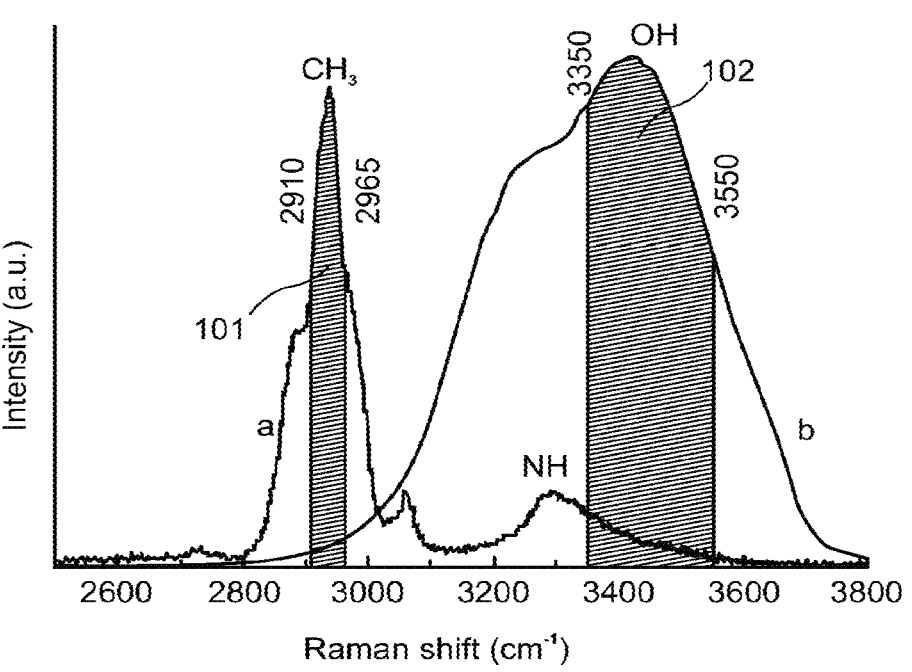
FIG. 1a shows a known plot of known Raman spectra.
Figure 1B:
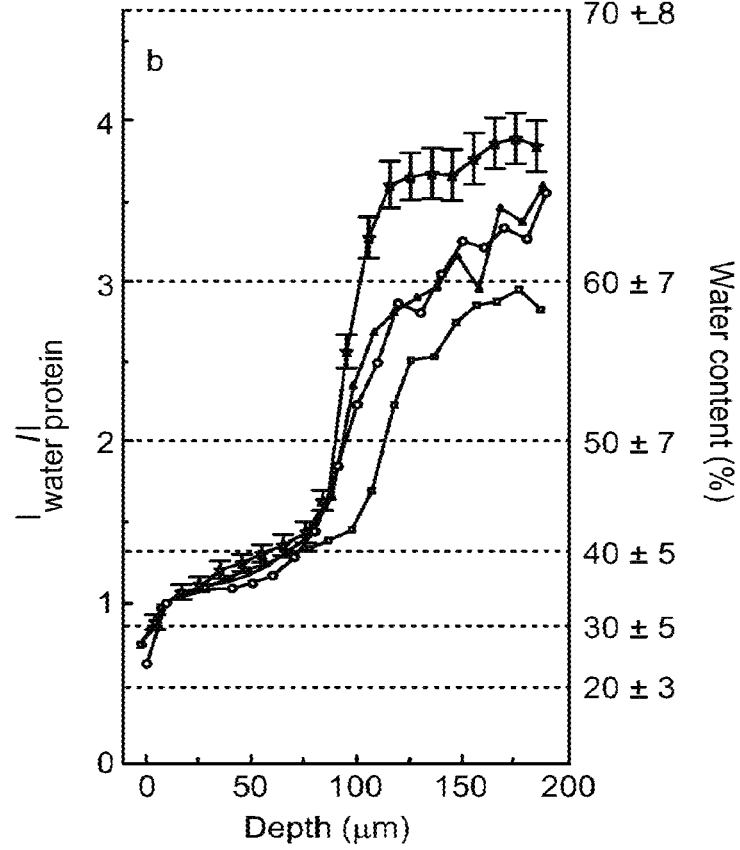
FIG. 1b shows a known plot of OH/CH₃ intensity ratios against skin depth.

FIG. 1*a*, taken from Caspers 2001, indicates known Raman spectra of a probed portion of human skin showing peaks for $CH_3$ and OH molecules. The areas 101, 102 below each peak between Raman shifts of 2910-2965 $cm^{-1}$ for $CH_3$ and 3350-3550 $cm^{-1}$ for OH give an approximation of the $CH_3$ and OH concentration intensities $I_{protein}$ and $I_{water}$. Such measurements may be made at different depth levels under the skin, for example from 0-200 μm, and may be used to provide $I_{water}/I_{protein}$ ratio values for a plurality of different skin depths. FIG. 1*b*, taken from Caspers 2001, shows an example plot of different $I_{water}/I_{protein}$ values against skin depth for a plurality of different locations on a patient's skin indicating water content percentage against skin depth. Each different symbol indicates a different skin location. A typical hydration value is around 60-85% water content, depending on the location of the measurement on the patient's skin. For a heavily dehydrated patient, the water content percentage may be less. For an overly hydrated patient it may be more.

As described above, a known diffraction grating based Raman spectrometer may be used to generate the full spectra shown in FIG. 1*a*. However, to calculate the $I_{water}/I_{protein}$ ratio values for a plurality of different skin depths, only the areas between Raman shifts of 2910-2965 $cm^{-1}$ for $CH_3$ and 3350-3550 $cm^{-1}$ for OH are of interest. Accordingly, as described in the aspects above, the present disclosure provides an optical module for Raman spectroscopy that is configured to detect a signal only in specific wavelength bandwidths of interest, for example, the areas 101, 102 corresponding to the wavelength band of $CH_3$ and OH molecules and to attenuate all other wavelengths of a Raman spectrum. The areas 101, 102 under the detected peaks are indicative of the intensities of the Raman scattering from the molecules of interest. The ratio of the two areas thus gives an indication of the relative concentration of OH to $CH_3$ molecules thus allows a hydration level, for example water content percentage, to be determined.

Figure 2A:
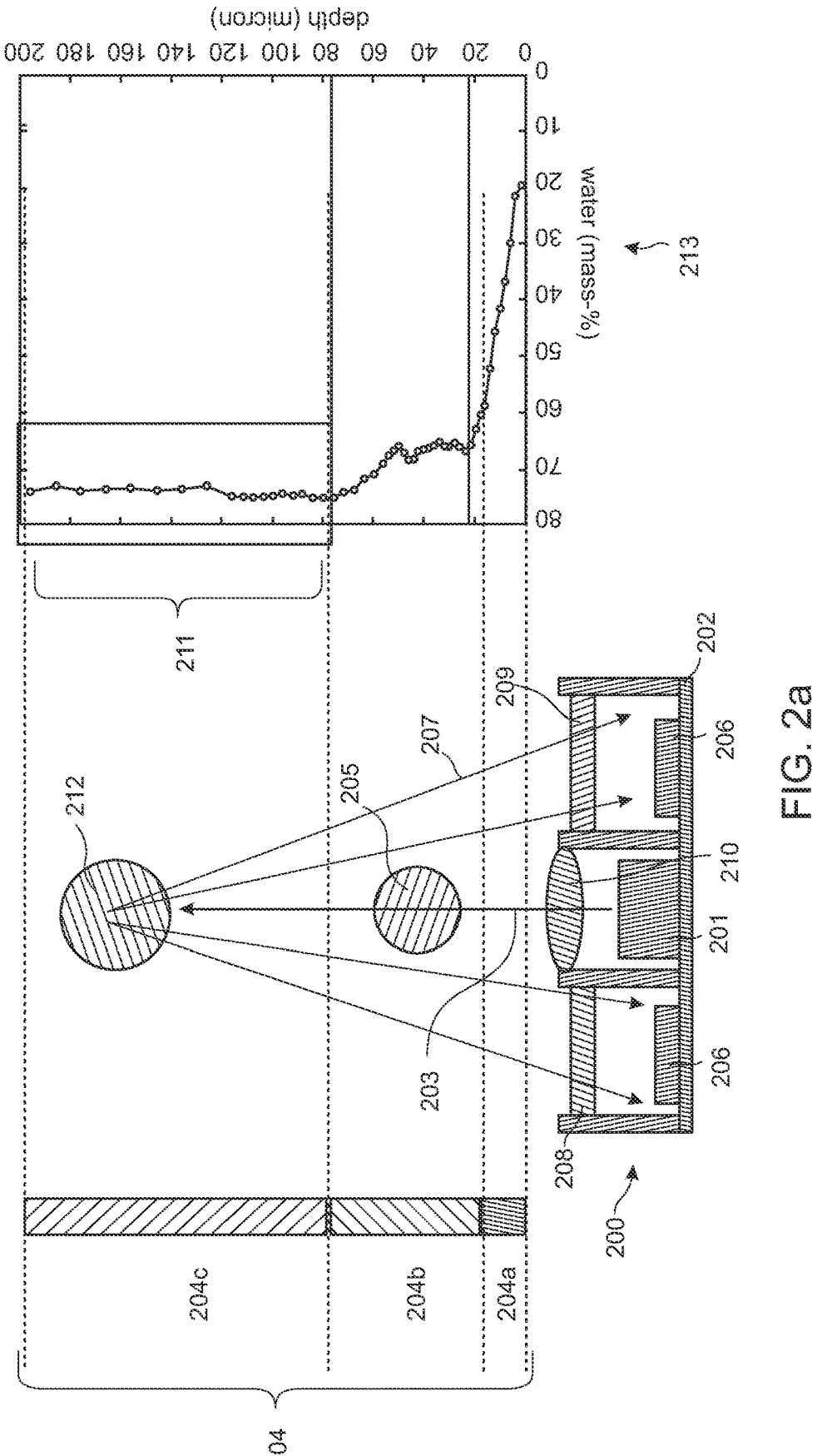
FIG. 2a illustratively shows an optical module according to the present disclosure.

FIG. 2*a* shows an optical module 200 according to the present disclosure. The optical module comprises a laser source 201 mounted on a substrate 202 and configured to emit electromagnetic radiation 203, for example at a wavelength of between 600-785 nm (although 500-900n, is also envisaged), at a target 204. Where the target is human skin, the skin may comprise multiple layers including an epidermis layer 204*a*, a pigment layer 204*b* and a dermis layer 204*c*. The electromagnetic radiation 203 emitted by the laser source 201 may cause fluorescence 205, especially when it propagates through the epidermis layer 204*a* or pigment layer 204*b*.

The optical module 200 further comprises a plurality of sensors 206 mounted on the substrate 203 and configured to detect electromagnetic radiation 207 scattered from the target 204. The optical module 200 further comprises first and second filters 208, 209 disposed over the sensors 206. The first filter 208 is substantially transparent to a first wavelength band corresponding to a Raman scattering wavelength of a first molecule of the target 204 and opaque to wavelengths outside the first wavelength band. The first wavelength band may correspond to the wavelength band corresponding to a Raman shift between 3350-3550 $cm^{-1}$ for OH molecules. The second filter 209 is substantially transparent to a second wavelength band corresponding to a Raman scattering wavelength of a second molecule of the target 204 and opaque to wavelengths outside the second wavelength band. The second wavelength band may correspond to the wavelength band corresponding to a Raman shift between 2910-2965 $cm^{-1}$ for $CH_3$ molecules.

Figure 5A:
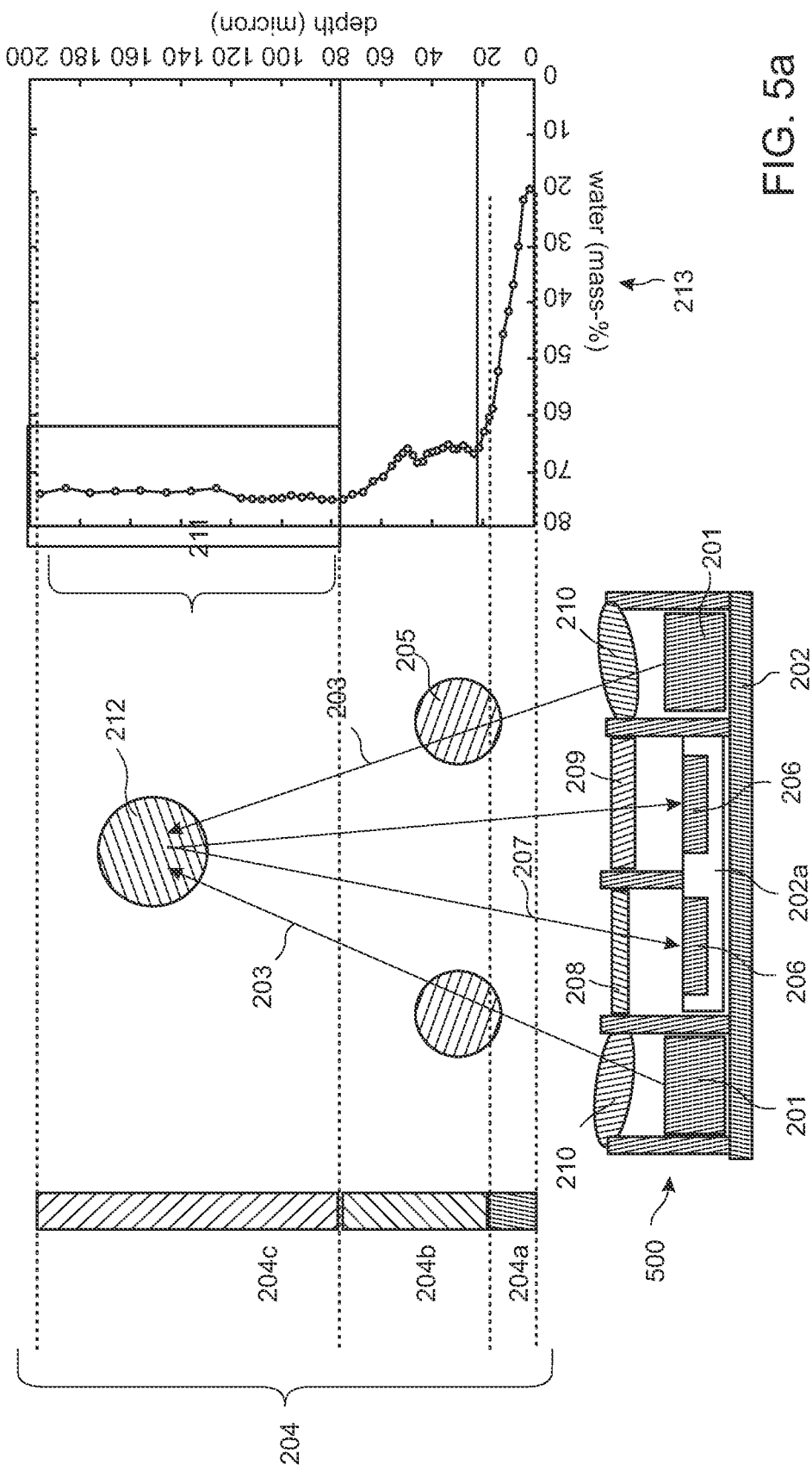
FIG. 5a illustratively shows an optical module according to the present disclosure.
Figure 5B:
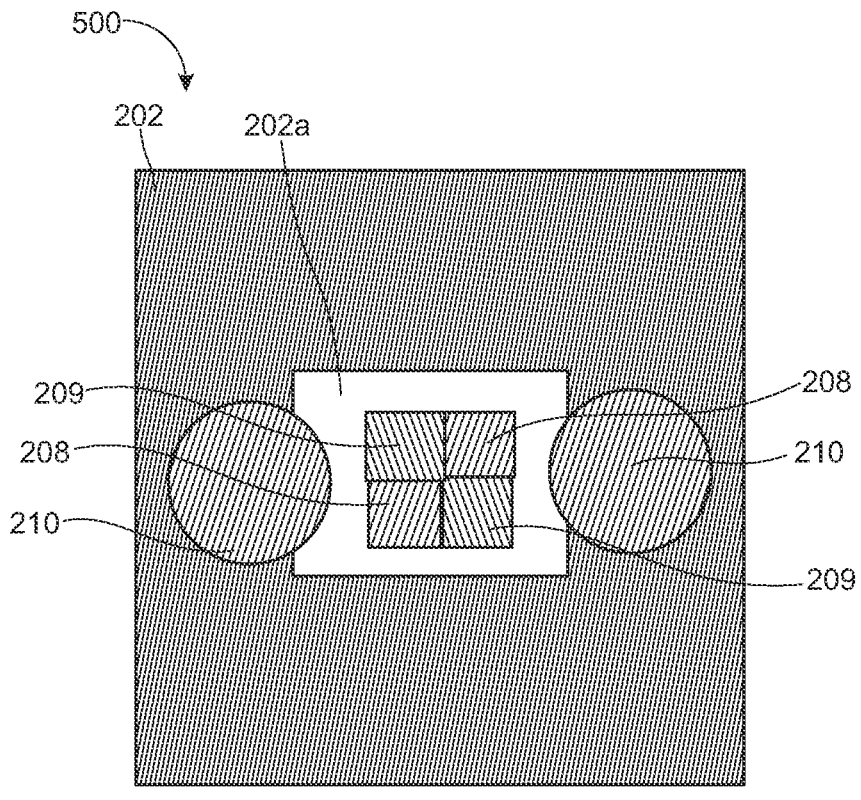
FIG. 5b illustratively shows a top view of an optical module according to the present disclosure.
Figure 5C:
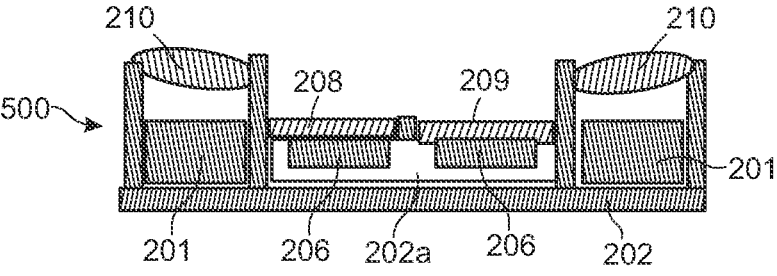
FIG. 5*c* illustratively shows an optical module according to the present disclosure.

As will be described below, the first and second filters 208, 209 (and any other filters that may be present) may be an integrated part of the detecting sensor ASIC where present such as shown in FIG. 5*c*.

The optical module 200 shown in FIG. 2 is also provided with a lens. This can be a fix lens focusing on 1 depth in the skin. It can be a lens 210 positioned in the optical path from the laser source 201 to the target 204, the lens 210 being configured to focus the electromagnetic radiation 203 emitted by the laser source 201 onto a plurality of focal points at respective depths 211 in a dermis layer 204*c* of the target 204.

In the example of FIG. 2*a*, the lens 210 also focusses the laser at points in the epidermis and pigment layer of the target, these points ranging between 0-200 μm below the surface of the skin. As described above, Raman scattering 212, for example a Stokes and/or anti-Stokes Raman shift, occurs from the OH molecules and $CH_3$ molecules at each of the probed depths 211. For each probe depth, a ratio of the OH molecule signal intensity (given by the area under the curve of the OH peak in the Raman shift spectrum as shown in FIG. 1*a*) to the $CH_3$ molecule signal intensity (given by the area under the curve of the $CH_3$ peak in the Raman shift spectrum as shown in FIG. 1*b*) may be calculated and plotted 213 against depth. The ratio values are indicative of the water content percentage present at each probed depth and resulting plot 213 thus provides a hydration profile of the target across the probed depths between 0-200 μm. The plot 213 shown in FIG. 2*a* illustrates the epidermis layer 204*a* and pigment layer 204*b* have low water content percentages ranging between approximately 20-70% which increases at the dermis layer 204*c* to above 70%. The water content percentage of the dermis layer may be used to determine whether a patient or user is over, under or normally hydrated in accordance with the methods of Caspers 2001. The inventors have found that the optical modules of the present disclosure have a water content percentage accuracy of better than +/−2%, for example typically +/−1.0% thus allowing hydration levels to be determined to a greater degree of accuracy than known methods such as urine colour tests, body weight loss measurements and/or Fresenius device measurements.

Figure 2B:
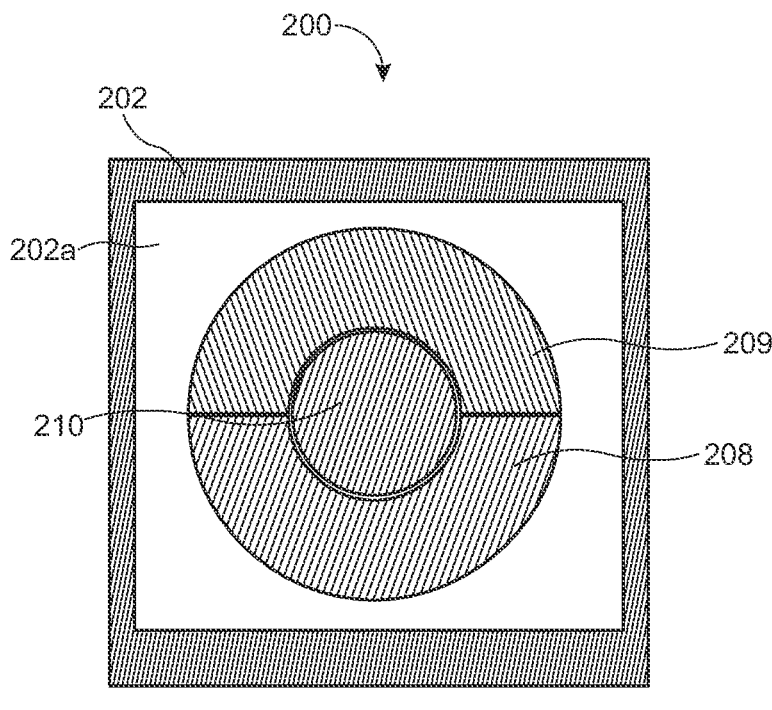
FIG. 2b illustratively shows a top view of an optical module according to the present disclosure.
Figure 2C:
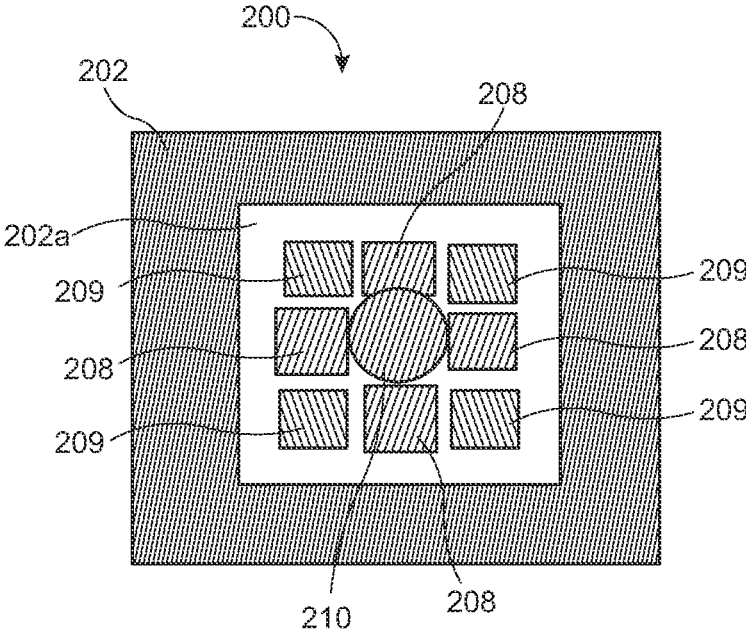
FIG. 2c illustratively shows a top view of an optical module according to the present disclosure.

FIGS. 2*b* and 2*c* show top views of two exemplary arrangements of the optical module 200 of FIG. 2*a* according to the present disclosure. Like-numbered elements are indicated by like reference numerals.

In FIG. 2*b*, the plurality of sensors 206 (not shown) are arranged in a circular pattern on the substrate 202 around the centrally positioned laser source 201 (not shown). The first and second filters 209, 208 disposed over or integrated with the sensors 206 accordingly form a ring-like shaped filter surrounding the lens 210 positioned in the optical path from the laser source 201 to the target 204. One half of the ring-like shaped filter is transparent to the first wavelength band and the other half of the ring-like shaped filter is transparent to the second wavelength band. The optical module 200 shown in FIG. 2b also comprises an application specific integrated circuit (ASIC) 202a onto which the plurality of sensors 206, filters 208, 209 and/or laser source 201 may be mounted and/or integrated thereby advantageously providing a fully integrated, miniaturised Raman spectroscopy solution without requiring a diffraction grating or external processing or data analysis of known benchtop devices. Integrating the plurality of sensors 206 with an ASIC 202a not only provides a cheaper, smaller, more easily manufactured Raman spectrometer but also provides improved noise reduction advantages by reducing parasitics of otherwise more complex optical setups and electronic circuits of known Raman spectrometers. The integration thus allows a trade off in optical resolution to be made for improved sensitivity. In turn, this improved sensitivity is one factor that allows the relatively weaker Raman scattering signals to be detected without the need to use a diffraction grating. Accordingly, there is a synergy between integrating the plurality of sensors 206 with an ASIC 202a and the ability to provide Raman spectroscopy without needing to use a diffraction grating.

In FIG. 2c, the plurality of sensors 206 (not shown are arranged in a pattern on the substrate around the centrally positioned laser source 201 (not shown). Unlike in FIG. 2b, the first and second filters 208, 209 are disposed over the plurality of sensors 206, for example integrated with the ASIC 202a over the sensor diodes of the ASIC 202a, in an alternating grid like manner. For example, each alternating sensor or group of sensors has either a first filter 208 or a second filter 209 disposed thereover, for example in the manner of a Bayer filter. As described below, the filters 202 may be dichroic filters integrated with the ASIC 202a, over the sensor diodes of the ASIC 202a. The number and arrangement of first and second filters shown in FIG. 2c is exemplary only and other arrangements, numbers and patterns of first and second filters are envisaged, including arrangements of filters integrated with the sensor diodes of the ASIC 202a.

Figure 3A:
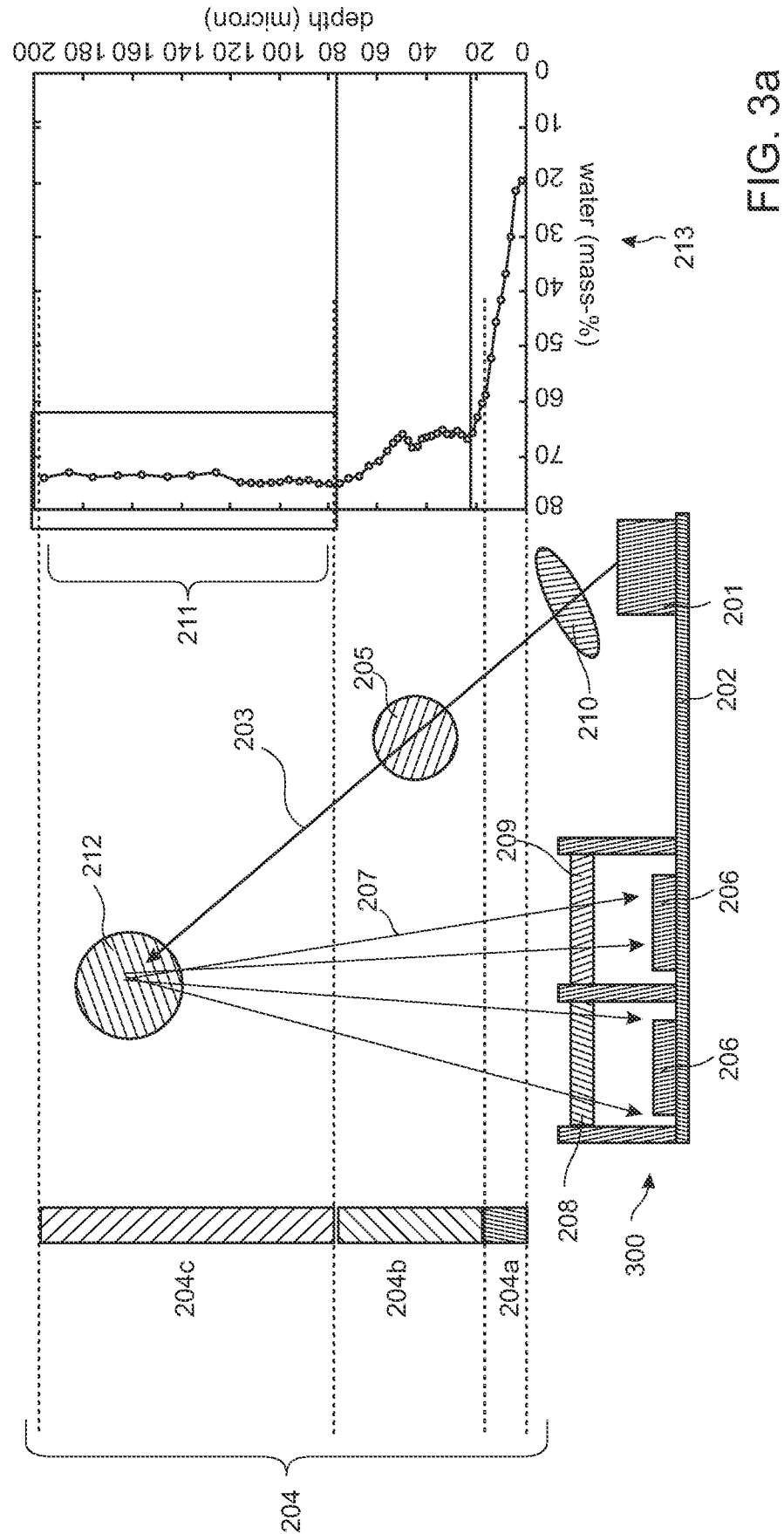
FIG. 3a illustratively shows an optical module according to the present disclosure.

FIG. 3a shows an optical module 300 according to the present disclosure that corresponds to the optical module 200 of FIG. 2a except for as described below. Like-numbered elements are indicated by like reference numerals. As with the optical module of FIG. 2a, the optical module 300 comprises a laser source 201 mounted on a substrate 202 and configured to emit electromagnetic radiation 203 at a target 204 through, for example, an epidermis layer 204a, a pigment layer 204b and a dermis layer 204c. Raman scattering 212 from known molecules such as OH and CH$_3$ molecules occurs in the target 204 and the electromagnetic radiation 207 scattered from the target 204 is detected in sensors 206 positioned behind filters 208, 209. Unlike in FIG. 2a, the laser source 201, and the optional lens 210, is positioned spaced apart from the plurality of sensors 206 on the substrate (and their respective filters 208, 209) and thus outside of the optical path of the scattered electromagnetic radiation 207. To achieve this, the laser source 201 is configured to emit electromagnetic radiation out of the optical module at the target at an angle relative to the plane of the substrate, for example in a direction non-perpendicular to the plane of the substrate. Advantageously, by positioning the laser source in this way, any fluorescence 205 that occurs from the pigment layer 204b that may have increased noise in the detected signal originates in a portion of the pigment layer 204b positioned further away from the plurality of sensors 206. This weakens any fluorescence 205 noise compared to a setup such as in FIG. 2a where the laser source is positioned among the sensors 206 or in setups such as in FIG. 4 where the emitted and scattered electromagnetic radiation 203, 207 share optical paths to and from the target 204. The further the laser source 201 is positioned from the sensors and the shallower the emission angle relative to the substrate, the further the emitted and scattered optical paths will be from each other as they pass through the pigment layer 204b and the weaker any fluorescence 205 detected by the sensors 206 will be.

Figure 3B:
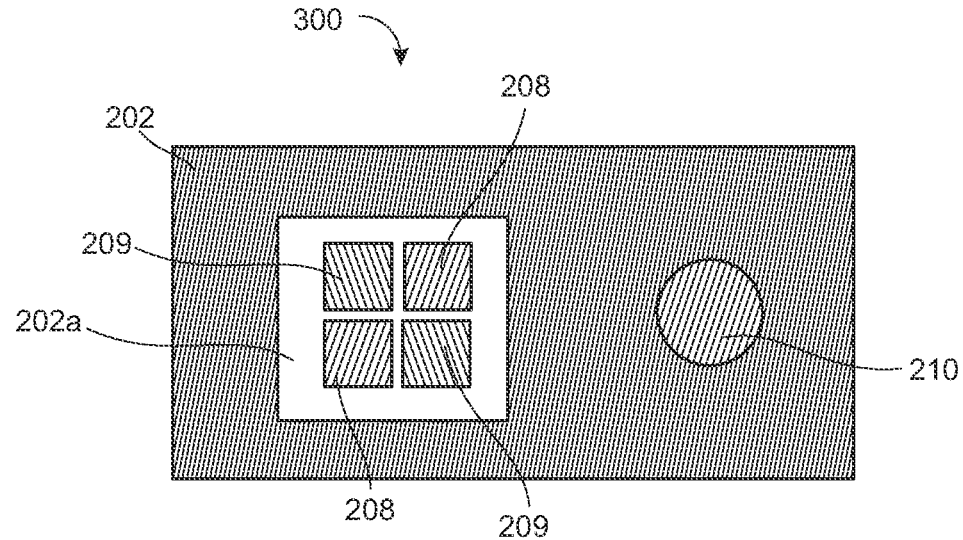
FIG. 3b illustratively shows a top view of an optical module according to the present disclosure.

FIG. 3b illustratively shows a top view of an optical module 300 according to the present disclosure. Like-numbered elements are indicated by like reference numerals. The optical module 300 corresponds to the optical module shown in FIG. 3a and the positioning of the laser source 201 laterally away from the plurality of sensors 206 on the substrate is illustrated.

Figure 4:
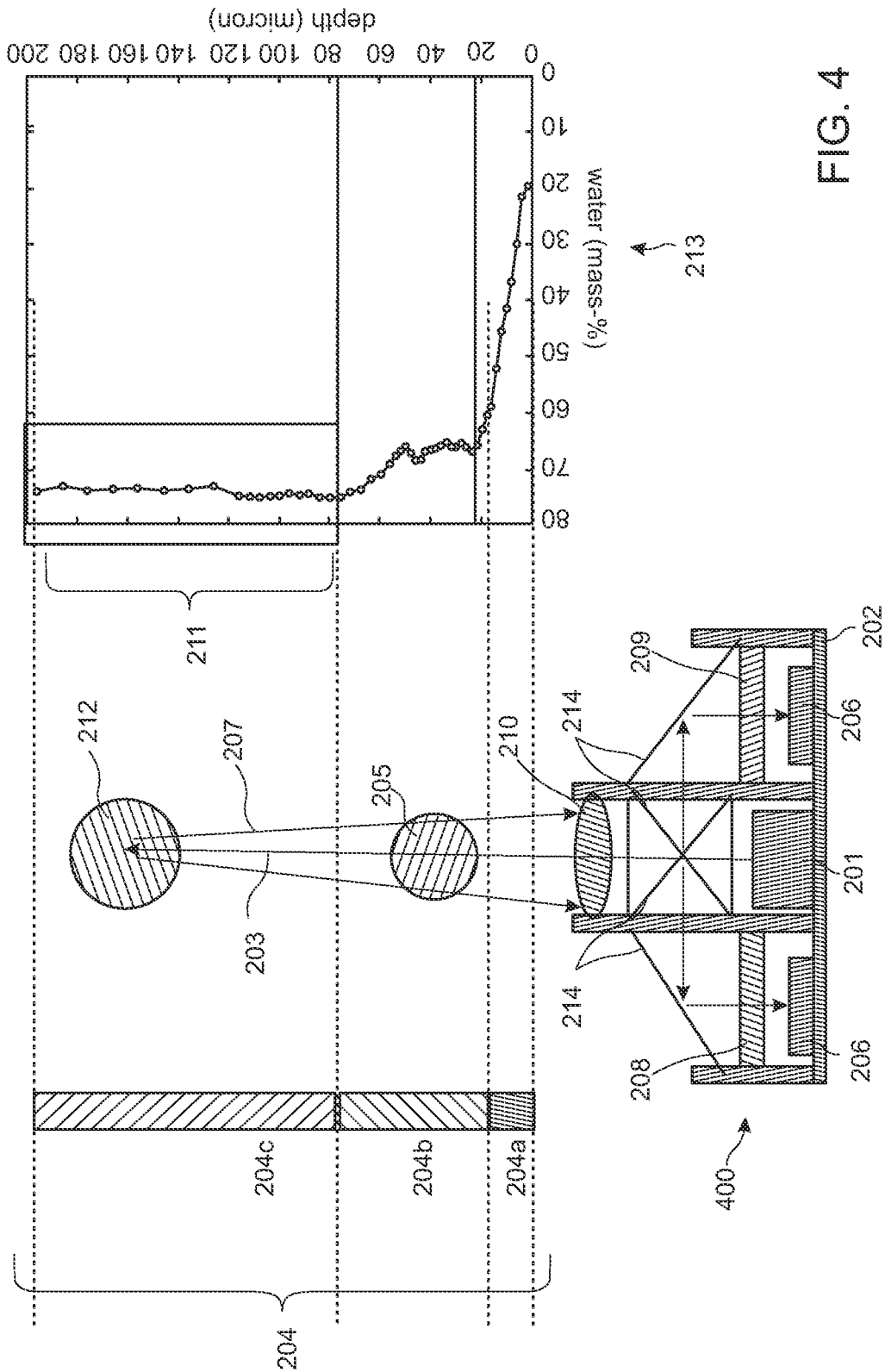
FIG. 4 illustratively shows an optical module according to the present disclosure.

FIG. 4 shows an optical module 400 according to the present disclosure that corresponds to the optical module 200 of FIG. 2a except for as described below. Like-numbered elements are indicated by like reference numerals. As with the optical module of FIG. 2a, the optical module 300 comprises a laser source 201 mounted on a substrate 202 and configured to emit electromagnetic radiation 203 at a target 204 through, for example, an epidermis layer 204a, a pigment layer 204b and a dermis layer 204c. Raman scattering 212 from known molecules such as OH and CH$_3$ molecules occurs in the target 204 and the electromagnetic radiation 207 scattered from the target is detected in sensors 206 positioned behind filters 208, 209. Unlike in the optical modules of FIGS. 2 and 3, the lens 210 of the optical module 400 of FIG. 4 is positioned in the optical path from the target to the plurality of sensors 206 whereby the electromagnetic radiation 203 emitted by the laser source 201 and the scattered electromagnetic radiation 207 propagate through the lens 210. Advantageously, the lens thus not only focusses the electromagnetic radiation 203 emitted by the laser source 201 but also functions as a collector for the scattered electromagnetic radiation 207. The optical module of FIG. 4 further comprises a plurality of reflectors, for example mirrors, 214 positioned in the optical path from the target 204 to the plurality of sensors 206 configured to direct the electromagnetic radiation 207 scattered form the target 204 to the plurality of sensors 206 through the first and second filters 208, 209. The optical module 400 of FIG. 4 may have the filter and lens arrangement as described in connection with FIGS. 2b and 2c.

FIG. 5a shows an optical module 500 according to the present disclosure that corresponds to the optical module 200 of FIG. 2a except for as described below. Like-numbered elements are indicated by like reference numerals. The optical module 500 of FIG. 5a comprises a plurality of laser sources 201 mounted on a substrate 202, for example two laser sources 201. As in FIG. 2a, each laser source 201 is configured to emit electromagnetic radiation 203 at a target 204 through, for example, an epidermis layer 204a, a pigment layer 204b and a dermis layer 204c. Raman scattering 212 from known molecules such as OH and CH$_3$ molecules occurs in the target 204 and the electromagnetic radiation 207 scattered from the target is detected in sensors 206 positioned behind first and second filters 208, 209, optionally on an ASIC 202a. The plurality of filters 208, 209 may be integrated and be part of the ASIC 202a as is shown in FIG. 5c. Advantageously, by using multiple laser sources, the power of each laser source may be reduced to stay within regulatory limits to avoid burning or damaging the target 204 whilst retaining the ability to focus sufficient power at a plurality of focal points in the dermis layer 204c to obtain a reliable Raman scattering 212 signal. The optical module 500 of FIG. 5a may also comprise a plurality of lenses positioned in the respective optical paths from the laser sources 201 to the target 204 and configured to focus the emitted electromagnetic radiation 203 onto a plurality of focal points at a plurality of depths in the dermis layer 204c of the target 204.

Advantageously, the plurality of laser sources 201 are arranged on either side of the plurality of sensors 206 that are positioned centrally on the substrate. As with the optical module 300 of FIG. 3a where the laser sources are laterally spaced apart from the sensors, this arrangement reduces the effect that any fluorescence may have on the detected signal as the fluorescence 205 is occurs in the target 204 at a position not above the sensors i.e. where the incident electromagnetic radiation 203 passes through the pigment layer 204b, rather than centrally where it may otherwise interfere with the Raman scattering 212 signal.

FIG. 5b shows a top view of an exemplary arrangement of the optical module 500 of FIG. 5a according to the present disclosure. Like-numbered elements are indicated by like reference numbers. The plurality of laser sources 201 (not shown) are under the plurality of lenses 210 on the substrate 202 in positions adjacent the centrally positioned plurality of sensors 206 (not shown) over which the first and second filters 208, 209 are disposed. As in FIGS. 2b and 2c, the optical module 500 may be provided with a grid-like array arrangement of first and second filters 208, 209, for example a 2×2, 4×4, 5×5, 6×6 array. The plurality of sensors 206 may also be mounted on an ASIC 202a as described above. The plurality of filters 208, 209 may be integrated on the ASIC on top of the sensors 206 as is shown in FIG. 5c.

FIG. 5c shows an optical module 500 according to the present disclosure corresponding to the optical module 500 of FIGS. 5a and 5b. Like-numbered elements are indicated by like reference numerals. In FIG. 5c, the filters 208, 209 are illustrated integrated with the ASIC 202a, for example integrated on the sensor diodes of the ASIC 202a. The ASIC 202a may thus be manufactured as a separate, general-use optoelectronic device with the filters 208, 209 integrated thereon during said manufacturing to provide a general-use integrated spectral sensor with built-in filters. When the optical module for Raman spectroscopy of the present disclosure is manufactured, the pre-built, general-use integrated spectral sensor may thus be used to reduce costs and simplify design and assembly requirements.

Figure 6A:
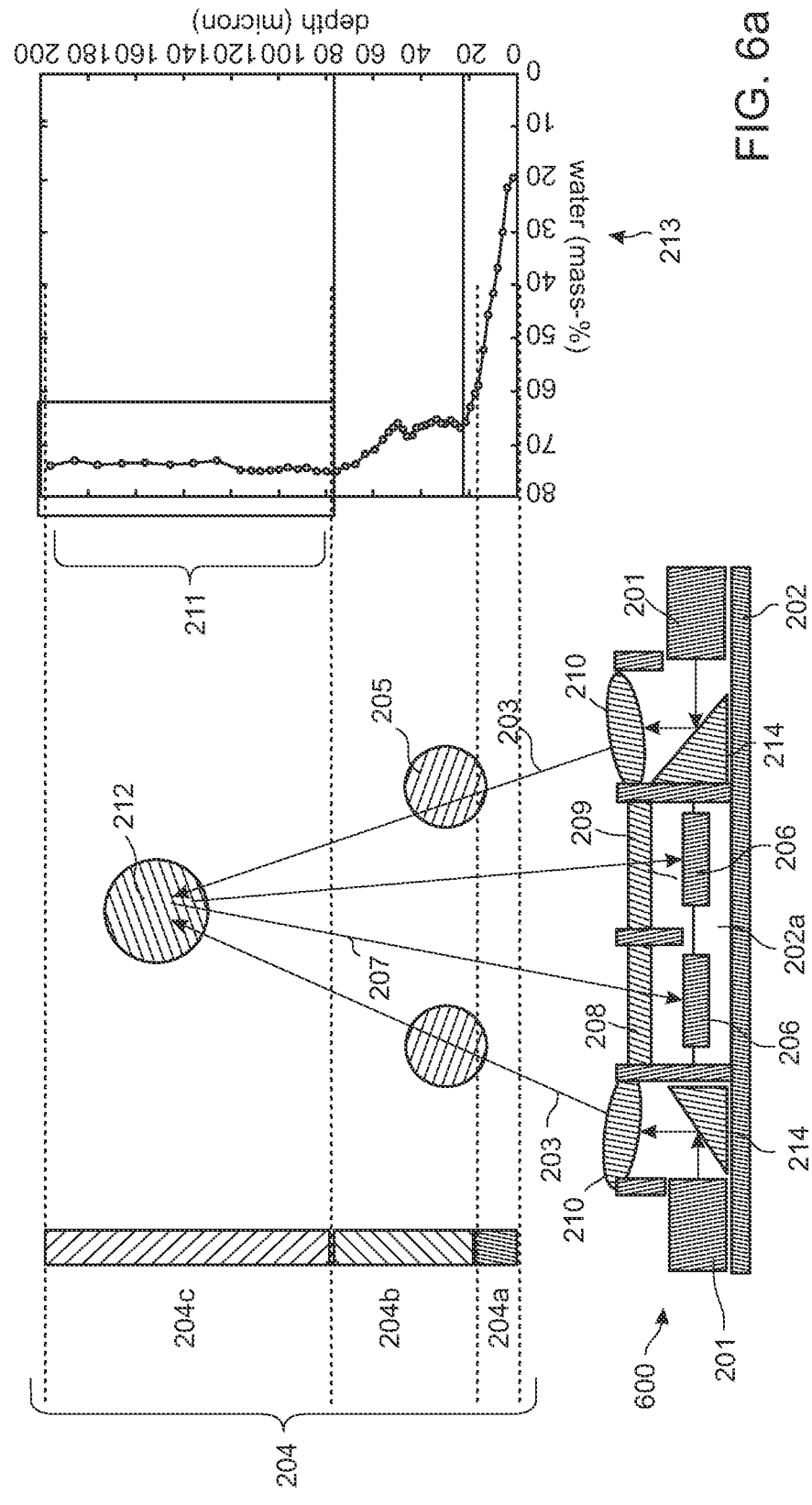
FIG. 6*a* illustratively shows an optical module according to the present disclosure.

FIG. 6a shows an optical module 600 according to the present disclosure that corresponds to the optical module 200 of FIG. 5a except for as described below. Like-numbered elements are indicated by like reference numerals. The optical module 600 of FIG. 5a comprises a plurality of laser sources 201 mounted on a substrate 202. As in FIG. 5a, each laser source 201 is configured to emit electromagnetic radiation 203 at a target 204 through, for example, an epidermis layer 204a, a pigment layer 204b and a dermis layer 204c. Raman scattering 212 from known molecules such as OH and CHs molecules occurs in the target 204 and the electromagnetic radiation 207 scattered from the target is detected in sensors 206 positioned behind first and second filters 208, 209, optionally on an ASIC 202a. Unlike in FIG. 5a, the optical module 600 of FIG. 6a comprises a plurality of reflectors 214 arranged in the optical path from the laser sources 201 to the target 204.

Advantageously, the plurality of optical reflectors 214 of FIG. 6a allow fewer laser sources 201 to be used than the optical module of FIG. 5a. For example, whilst not shown in FIG. 6a, the electromagnetic radiation from a single laser source 201 may be split multiple times and directed with the reflectors 214 to each of the lenses 210. Reducing the number of laser sources 201 (such as edge emitters or VCSELs) makes the optical module 600 cheaper and simpler to manufacture. The use of a plurality of reflectors 214 also allows the laser sources to be positioned elsewhere on the substrate than disposed under the lenses thereby allowing a greater degree of customizability of the optical module lay out. For example, the vertical height of the optical module may be reduced as the laser sources need no longer fit under the lenses thus allowing the optical module to be reduced in size and miniaturized in the vertical direction.

Figure 6B:
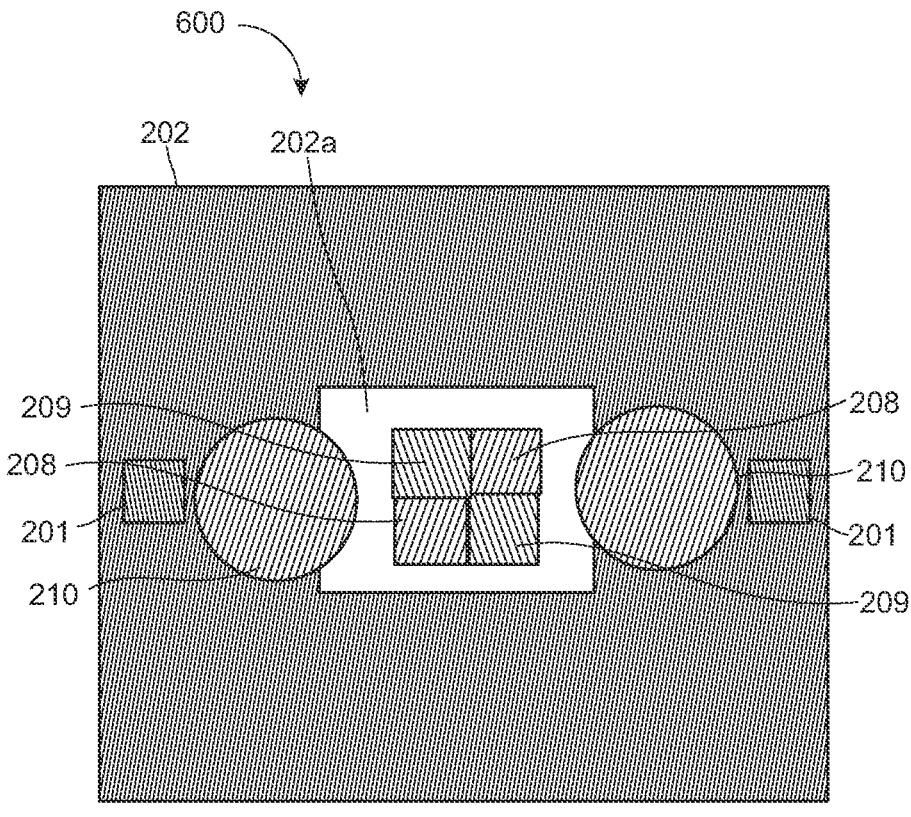
FIG. 6*b* illustratively shows a top view of an optical module according to the present disclosure.

FIG. 6b shows a top view of an exemplary arrangement of the optical module 600 of FIG. 6a according to the present disclosure. Like-numbered elements are indicated by like reference numbers. The arrangement is the same as that shown in FIG. 5b except that the plurality of reflectors 214 are disposed under the lenses and allow fewer laser sources 201 as described above. The example of FIG. 6b has two laser sources 201 arranged on the ASIC 202a on either side of the sensors 206. The reflectors 214 positioned under the lenses direct the laser beams through the lenses 210.

Figure 7A:
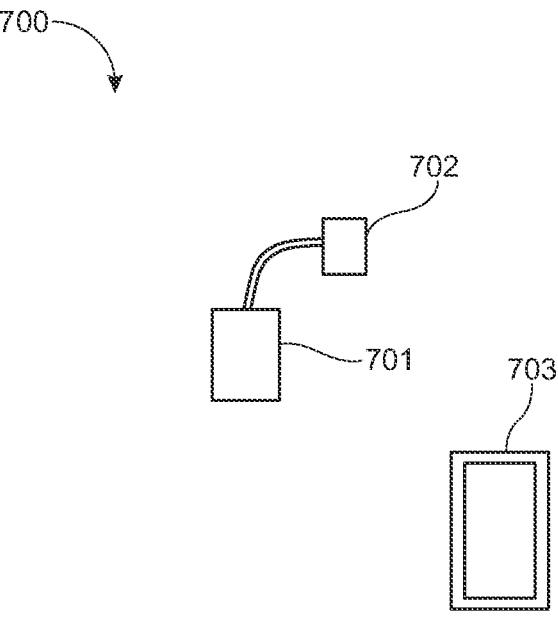
FIG. 7*a* illustratively shows a Raman spectrometer according to the present disclosure.

FIG. 7a shows a portable Raman spectrometer 700 comprising an optical module 200, 300, 400, 500, 600 of any of the embodiments described above and a mounted at a forward end 701 of the spectrometer 700. The Raman spectrometer 700 is provided with a computer-readable storage medium (not shown) having stored thereon instructions which, when the instructions are executed by a processor, for example a processor of the Raman spectrometer, cause the processor to carry out the method of determining relative concentrations of first and second known molecules of a target as described herein. Optionally, the Raman spectrometer 700 is provided with a USB rechargeable battery. Advantageously, the power requirements of the optical module of the present disclosure is reduced compared to known Raman spectrometers to the miniaturisation of the optical module components. Accordingly, the battery life may be sufficient for Raman measurements at intervals of 5-10 minutes continuously for one week. The Raman spectrometer may be configured to be Bluetooth and/or WiFi compatible to communicate with another smart device such as a smart phone 703, be provided with a display device such as a display screen on which to display hydration levels over time and/or be provided with a memory to store logged values of continuous measurements while the device is being used.

Figure 7B:
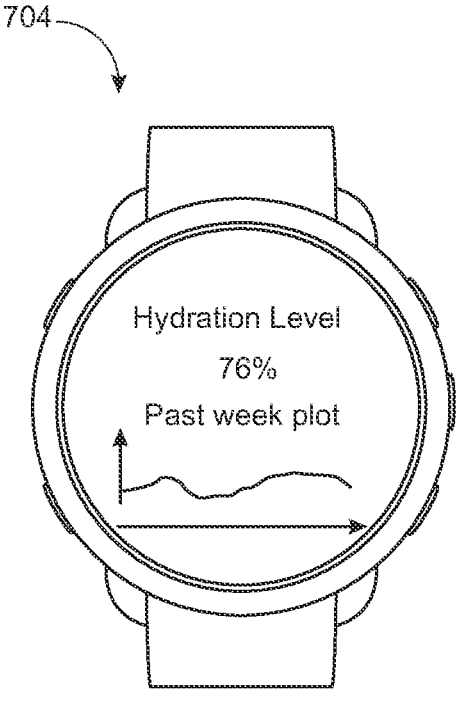
FIG. 7*b* illustratively shows a wearable device according to the present disclosure.

FIG. 7b shows a wearable device 704 comprising an optical module 200, 300, 400, 500, 600 of any of the embodiments described above and a mounted on a skin facing side of the wearable device 704, as with the portable Raman spectrometer of FIG. 7a, The wearable device 704 is provided with a computer-readable storage medium (not shown) having stored thereon instructions which, when the instructions are executed by a processor, for example a processor of the wearable device, cause the processor to carry out the method of determining relative concentrations of first and second known molecules of a target as described herein. Advantageously, the power requirements of the optical module of the present disclosure is reduced compared to known Raman spectrometers to the miniaturisation of the optical module components. Accordingly, the battery life may be sufficient for Raman measurements at intervals of 5-10 minutes continuously for one week. The wearable device 704 may be configured to be Bluetooth and/or WiFi compatible to communicate with another smart device such as a smart phone, be provided with a display device such as a display screen on which to display hydration levels over time and/or be provided with a memory to store logged values of continuous measurements while the device is being used. The wearable device 704 illustrated in FIG. 7*b* comprises a smart watch worn on a forearm or wrist. As described above, the wearable device may comprise a smart watch, a heartrate monitor and/or a pulse oximeter. Where the present disclosure is provided as a dedicated hydration level monitor, the hydration level monitor may take the same or similar structures as the above described wearable devices except be provided solely with hydration level monitoring functionality.

FIG. 8 is a flowchart of a method 800 according of determining relative concentrations of first and second known molecules of a target, for example using the optical module of any of the embodiments herein. The method comprises, with a laser source mounted on a substrate, emitting 801 electromagnetic radiation at a target. With a plurality of sensors mounted on the substrate, detecting 802 electromagnetic radiation scattered from the target, wherein first and second filters are disposed over the sensors, the first filter substantially transparent to a first wavelength band corresponding to a Raman scattering wavelength of the first molecule and opaque to wavelengths outside the first wavelength band, and the second filter substantially transparent to a second wavelength band corresponding a Raman scattering wavelength of the second molecule and opaque to wavelengths outside the second wavelength band. Calculating 803 a ratio between intensities of the Raman scattering from the first and second molecules, and determining 804 a relative concentration of the first molecule to the second molecule from the ratio.

Although the present disclosure has been described in terms of preferred embodiments as set forth above, it should be understood that these embodiments are illustrative only and that the claims are not limited to those embodiments. Those skilled in the art will be able to make modifications and alternatives in view of the disclosure that are contemplated as falling within the scope of the appended claims. Each feature disclosed or illustrated in the present specification may be incorporated in the invention, whether alone or in any appropriate combination with any other feature disclosed or illustrated herein.

For example, whilst the term mounted on has been used herein in connection with the sensors and laser sources being mounted on a substrate, it is envisaged that this includes incorporated and/or integrated the sensors and/or laser sources with the substrate and/or ASIC if present as part of a die manufacturing process.

For example, whilst the above disclosure has been described in the context of determining hydration by determining a ratio of OH and CH₃ molecule concentrations in a dermis layer, it is envisaged that all embodiments may be used to determine the ratio of any molecules or groups of molecules where a full molecular profile is not desired whether in the context of hydration measurements or otherwise. For example, the present disclosure may thus find applications in assessing blood glucose levels, and concentrations of pharmacological compounds, recreational drugs, and other substances. Similarly, various relative molecule concertation profiles of other layers of the skin or body may also be determined, for example, profiles of the epidermis layer, pigment layer, and/or layers deeper in the body. Thus the present disclosure provides an optical module for Raman spectrometry for any application where a miniaturized Raman spectrometer and ratios of specific known molecule concentrations are desired.

The present disclosure also envisages determining a ratio of concentrations of more than two molecules. For example, by incorporating additional filters into all embodiments transparent only to wavelength bands corresponding to the Raman scattering wavelength of the additional known target molecules. Thus as long as the target molecule Raman scattering wavelengths are known in advance and a full molecular profile is not required, Raman spectroscopy may be performed with the present, miniaturized optical module without a diffraction grating.

The present disclosure also envisages that, depending on the Raman excitation energies of the target molecules, multiple laser sources may be used with all the above embodiments to excite the target at multiple wavelength bands. Thus whilst multiple laser sources having emission wavelengths of at or between the narrowband values of 600 nm and 785 nm are described above, other wavelengths and wavelength bands are also envisaged. For example, each laser source of the plurality of laser sources may have a different wavelength.

The present disclosure also envisages that, in order to provide a fully miniaturized and integrated solution, the laser sources of all embodiments may comprise a laser diode, edge emitter, or vertical cavity surface emitting lasers (VCSEL) integrated with the substrate during a die manufacturing process. Similarly, the one or more sensors of the plurality of sensors may comprise a photo diode, a single photon avalanche diode (SPAD), an avalanche photo diode, a silicon photomultiplier (SiPM), a charge coupled device (CCD), or a MEMS photomultiplier integrated with the substrate, and/or ASIC if present. Advantageously, these components may easily be integrated with or in the substrate to further enhance the ease at which the device of the present disclosure may be mass-produced in semiconductor device fabrication facilities in high volumes compared to known Raman spectrometers which often require manual assembly which is slower and more expensive.

The present disclosure also envisages that, for all embodiments, the first and second filters may comprise multiple layers of filters, each filter may comprise two filters layered on top of each other, to ensure such noise and signals from other molecules which are not molecules are interest are strongly attenuated and do not reach the plurality of sensors. For example, the first and second filters may comprise one or more dichroic filters and/or have an optical density value of between 10-12 for wavelengths outside the wavelength bands of interest.

The present disclosure also envisages that, when the plurality of sensors are mounted on an ASIC. The ASIC with the plurality of sensors thereon may be manufactured as a separate, general-use optoelectronic device and the filters integrated with the optoelectronic device, above the plurality of sensors, during said manufacturing thus providing a general-use integrated spectral sensor with built-in filters. When the optical module for Raman spectroscopy of the present disclosure is manufactured, the pre-built, general-use integrated spectral sensors with built-in filters may be mounted on a printed-circuit board with the laser sources and lenses thus further simplifying the assembly process of the present miniature Raman spectrometer. Alternatively, the filters may be provided separate to the general-use integrated spectral sensor.

The present disclosure also envisages that, for all embodiments, support structures may be used to position and enclose the components of the optical module on the substrate. Such support structures may be formed with, for example, injection molding and/or 3D printing and/or may be machined to alter their dimensions during optical calibration of the device. Such support structures may be opaque to electromagnetic radiation to ensure environmental noise at the plurality of sensors is reduced.

The present disclosure also envisages that, for all embodiments, the optical module may have a volume of under 2 $cm^3$, for example between 1-2 $cm^3$ or even 20-100 $mm^3$ made possible by omission of the diffraction grating of known Raman spectrometers, thus allowing the optical module to be incorporated into portable and/or wearable devices such as smart watches, smart phones, heart rate monitors, and other vital sign monitors in point-of-care environments and/or sport settings. Similarly, the optical module may be incorporated into mobile devices such as smart phones and/or into attachments for mobile devices. Thereby making such devices Raman spectroscopy capable for the above described and other use cases where relative concentrations of specific, known molecules are required.

The term integrated circuit as used herein may refer to a set of electronic circuits integrated on semiconductor substrate thereby forming a microchip wherein all the circuit elements are inseparably associated and electrically interconnected so that the integrated circuit is considered to be indivisible as will be appreciated by the skilled person. The integrated circuit may in some implementations comprise a general purpose processor which is in contrast to the implementations provided with an application specific integrated circuit which refers to an integrated circuit customized for the particular use specified herein.

REFERENCE NUMERAL LIST 101 area of OH molecule Raman peak
102 area of $CH^3$ molecule Raman peak
200 optical module according to the present disclosure
201 laser source
202 substrate
202*a* ASIC
203 emitted electromagnetic radiation
204 target
204*a* epidermis layer
204*b* pigment layer
204*c* dermis layer
205 fluorescence
206 plurality of sensors
207 scattered electromagnetic radiation
208 first filter
209 second filter
210 lens
211 plurality of depths in dermis layer
212 Raman scattering
213 plot of water content against target depth
214 plurality of reflectors
300 optical module according to the present disclosure
400 optical module according to the present disclosure
500 optical module according to the present disclosure
600 optical module according to the present disclosure
700 Raman spectrometer according to the present disclosure
701 forward end of Raman spectrometer
702 rechargeable battery
703 smart device 704 wearable device
800 method according to the present disclosure
801 emitting electromagnetic radiation at a target
802 detecting electromagnetic radiation scattered from the target
803 calculating a ratio between intensities of Raman scattering from first and second molecules
804 determining a relative concentration of the first molecule to the second molecule form the ratio

The invention claimed is:

1. An optical module for Raman spectroscopy, the optical module comprising:
   a laser source mounted on a substrate and configured to emit electromagnetic radiation at a target;
   a plurality of sensors mounted on the substrate and configured to detect electromagnetic radiation scattered from the target;
   a first filter disposed over one or more of the plurality of sensors,
   wherein the first filter is substantially transparent to a first wavelength band corresponding to a Raman scattering wavelength of a first molecule of the target and opaque to wavelengths outside the first wavelength band;
   a second filter disposed over one or more of the plurality of sensors,
   wherein the second filter is substantially transparent to a second wavelength band corresponding to a Raman scattering wavelength of a second molecule of the target and opaque to wavelengths outside the second wavelength band; and
   a lens positioned in an optical path from the laser source to the target, the lens being configured to focus the electromagnetic radiation emitted by the laser source onto one or more focal points at respective depths in a dermis layer of the target,
   wherein the lens is positioned in the optical path from the target to the plurality of sensors.

2. The optical module of claim 1, comprising an integrated circuit mounted on the substrate.

3. The optical module of claim 2, wherein the integrated circuit is configured to control the laser source to emit modulated electromagnetic radiation at the target and to demodulate the detected electromagnetic radiation scattered from the target.

4. The optical module of claim 3, wherein the integrated circuit is an application specific integrated circuit (ASIC) and comprises said plurality of sensors, said first and second filters.

5. The optical module of claim 4, wherein the ASIC further comprises phase lock loop detection circuitry, signal amplification circuitry and laser source driving circuitry.

6. The optical module of claim 1, wherein the lens is positioned outside the optical path from the target to the plurality of sensors.

7. The optical module of claim 1, wherein the laser source is positioned spaced apart from the plurality of sensors on the substrate and is configured to emit electromagnetic radiation out of the optical module at the target in a direction non-perpendicular to a plane of the substrate.

8. The optical module of claim 1, wherein the optical module comprises a plurality of reflectors positioned in the optical path from the target to the plurality of sensors, the reflectors configured to direct the electromagnetic radiation scattered from the target to the plurality of sensors through the first and second filters.

9. The optical module of claim 1, comprising a plurality of said laser sources mounted on the substrate.

10. The optical module of claim 9, comprising a plurality of lenses positioned in respective optical paths of the laser sources and configured to focus the emitted electromagnetic radiation from the laser sources onto one or more focal points at a plurality of depths in a dermis layer of the target.

11. The optical module of claim 1, wherein the first and second filter respectively have an optical density value of between 10-12 for wavelengths outside the first and second wavelength bands.

12. The optical module of claim 1, wherein the electromagnetic radiation emitted by the laser source has a wavelength of between 600-785 nm;

wherein the first filter is transparent to a wavelength band corresponding to a Raman scattering wavelength of an OH molecule; and wherein the second filter is transparent to a wavelength band corresponding to a Raman scattering wavelength of a $CH_3$ molecule.

13. A method of determining relative concentrations of first and second known molecules of a target, the method comprising:

with a laser source mounted on a substrate, emitting electromagnetic radiation at a target, wherein a lens is positioned in an optical path from the laser source to the target, the lens being configured to focus the electromagnetic radiation emitted by the laser source onto one or more focal points at respective depths in a dermis layer of the target;

with a plurality of sensors mounted on the substrate, detecting electromagnetic radiation scattered from the target, wherein the lens is positioned in the optical path from the target to the plurality of sensors, and wherein first and second filters are disposed over the sensors, the first filter substantially transparent to a first wavelength band corresponding to a Raman scattering wavelength of the first molecule and opaque to wavelengths outside the first wavelength band, and the second filter substantially transparent to a second wavelength band corresponding a Raman scattering wavelength of the second molecule and opaque to wavelengths outside the second wavelength band; and calculating a ratio between intensities of the Raman scattering from the first and second molecules; and determining a relative concentration of the first molecule to the second molecule from the ratio.

14. The method of claim 13, comprising:

controlling the laser source to emit modulated electromagnetic radiation at the target; and demodulating the detected electromagnetic radiation scattered from the target.

15. The method of claim 13, wherein the emitted electromagnetic radiation has a wavelength of between 600-785 nm;

wherein the first filter is transparent to a wavelength band corresponding to a Raman scattering wavelength of an OH molecule; and wherein the second filter is transparent to a wavelength band corresponding to a Raman scattering wavelength of a $CH_3$ molecule.

16. The method of claim 15, wherein the first molecule is an OH molecule;

wherein the second molecule is a $CH_3$ molecule; and wherein the method comprises determining a hydration level of the target from the relative concentration of OH molecules to $CH_3$ molecules.

17. A Raman spectrometer a wearable device or a hydration level monitor comprising the optical module of claim 1.

\* \* \* \* \*